US00PP31494P2

(12) United States Plant Patent
Korlipara

(10) Patent No.: US PP31,494 P2
(45) Date of Patent: Feb. 25, 2020

(54) ***ECHINACEA* PLANT NAMED 'EMBERS SPARKS'**

(50) Latin Name: ***Echinacea* spp.**
Varietal Denomination: Embers Sparks

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/501,659

(22) Filed: May 17, 2019

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ..... A01H 5/02; A01H 6/14
See application file for complete search history.

*Primary Examiner* — Annette H Para
(74) *Attorney, Agent, or Firm* — Klarquist Sparkman, LLP

(57) ABSTRACT

A new and distinct *Echinacea* plant named 'Embers Sparks' characterized by an amazing number of large inflorescences starting in the first season, very upright, compact habit, bright yellow ray florets surrounding green-yellow cones, strong upright stems, and excellent vigor.

1 Drawing Sheet

Botanical denomination: *Echinacea* spp.
Variety designation: 'Embers Sparks'.

BACKGROUND OF THE INVENTION

The present invention relates to a new and distinct cultivar of *Echinacea* given the cultivar name 'Embers Sparks'. *Echinacea* is in the family Asteraceae. The exact parents of this selection are unknown, unnamed, proprietary interspecific hybrids bred from *Echinacea paradoxa, Echinacea purpurea*, and *Echinacea tennesseensis*. The new cultivar is part of a planned breeding program for container grown, well branched, compact, bright, long lasting flower color, and extended bloom time.

Compared to *Echinacea* 'Dixie Sun' (U.S. Plant Pat. No. 26,160), the new cultivar produces more crowns from the base more quickly and has more inflorescences per stem.

Compared to *Echinacea* 'Cleopatra' (U.S. Plant Pat. No. 24,631), the new cultivar has more stems per plant and is branched rather than non-branched.

Compared to *Echinacea* 'Mac 'n' Cheese' (U.S. Plant Pat. No. 19,464), the new cultivar has a shorter habit, more yellow-toned ray florets rather than orange, and a higher crown count.

Compared to *Echinacea* 'Matthew Saul' (U.S. Plant Pat. No. 17,652), the new cultivar has more inflorescences per stem and has more orange-toned ray florets rather than yellow.

Compared to *Echinacea* SOMBRERO® Granada Gold ('Balsomold'), U.S. Plant patent application Ser. No. 30,115, the new cultivar has less orange ray flowers.

Compared to *Echinacea* SOMBRERO® Lemon Yellow ('Balsomemy'), U.S. Plant Pat. No. 24,768, the new cultivar is more yellow rather than orange.

Compared to *Echinacea* 'Now Cheesier' (U.S. Plant Pat. No. 23,059), the new cultivar has less orange ray flowers, a more vigorous crown, and more inflorescences per stem.

SUMMARY OF THE INVENTION

The present invention has not been evaluated under all possible environmental conditions. The phenotype may vary with variations in environment without a change in the genotype of the plant.

*Echinacea* 'Embers Sparks' is uniquely distinguished by:

1. an amazing number of large inflorescences starting in the first season,
2. very upright, compact habit,
3. bright yellow ray florets surrounding green-yellow cones,
4. strong upright stems, and
5. excellent vigor.

This new cultivar has been reproduced only by asexual propagation (cuttings and tissue culture using shoot tips). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows an eight-month-old *Echinacea* 'Embers Sparks' in flower, growing in the trial field in full sun in mid-September in Canby, Oreg.

DETAILED PLANT DESCRIPTION

The following is a detailed description of the new *Echinacea* cultivar based on observations of 3-year-old specimens growing in the trial bed in full sun in Canby, Oreg.

Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart, 5th* edition, 2007.

Plant:

*Type*.—Herbaceous perennial.

*Hardiness*.—USDA Zones 4 to 9.

*Size*.—Grows to 48 cm wide and 54 cm tall to top of inflorescences.

*Form*.—Basal clump, with up to 14 crowns.

*Vigor*.—Excellent.

*Roots*.—Fibrous, with many downward growing and few laterals, ivory in color, Yellow White 158D, roots develop easily from cuttings from the crown.

Leaf (basal):

*Type*.—Simple.

*Shape*.—Lanceolate.

*Arrangement*.—Alternate.

*Blade size*.—Grows to 17 cm long and 4 cm wide.

*Margins*.—Sparsely serrate.

*Apex*.—Acuminate.

*Base*.—Attenuate.

*Surface texture*.—Both sides strigose.

*Venation*.—Pinnate.

*Variegation*.—Absent.

*Color*.—Green 137A with veins Green 145C on topside, Green 147B with veins Green 147C on bottom side; petiole clasping, to 8 cm long and 3 mm wide, strigose, Green 147C.

Leaf (stem):

*Type*.—Simple.

*Shape*.—Lanceolate.

*Arrangement*.—Alternate.

*Leaf number*.—60.

*Blade size*.—Grows to 14 cm long and 3.5 cm wide.

*Margins*.—Usually entire to sparsely serrate.

*Apex*.—Acuminate.

*Base*.—Attenuate.

*Surface texture*.—Strigose on both sides.

*Rugosity*.—Absent.

*Venation*.—Pinnate, Yellow Green 145C on both sides.

*Variegation*.—Absent.

*Color*.—Topside Green N137A, bottom side closest to Green 137B.

*Petiole description*.—Clasping, grows to 2 cm long and 7 mm wide, scabrous, narrow leafy edges, topside and bottom side Yellow Green 147C.

Inflorescence:

*Type*.—Daisy, composite on terminal stalked heads.

*Number of fully expanded flowers*.—Up to 80.

*Flowering stem*.—Grows to 23 cm tall from the base of the plant to the terminal leaves below peduncle; unbranched to branched, 3 to 7 inflorescences per stem; diameter growing to 10 mm wide near the inflorescence; strigose; strong; Yellow Green 147B.

*Size*.—Grows to 9 cm wide and 6.5 cm deep as disc enlarges.

*Form*.—Ray florets held horizontally when young, reflexing slightly when they mature, mature disc is conic.

*Peduncle*.—Grows to 27 cm long from above terminal leaves to flower, 4 cm wide, strigose; Yellow Green 147B.

*Peduncle strength*.—Strong.

*Immature inflorescence* (*bud*).—Up to 40, 4 cm wide and 3 cm deep, ray florets held upright at a 40 degrees angle from vertical and rolled up so only the back color shows, Yellow Orange 15B, disc color Yellow Green 144A.

*Ray florets*.—Without pistil or stamen, 21 to 26 in number, grow to 30 mm long and 9 mm wide, oblanceolate to lanceolate with the tip two-to-three-toothed (each acute), entire margins, base attenuate, glabrous on both sides, horizontal attitude at origin, drooping to semi-drooping near senescence; first and fully open florets topside closest to Yellow Orange 15B, bottom side 15D; florets lighten to topside Yellow 2D, bottom side between Yellow Green 150C and Yellow Green 150D.

*Disc*.—Flat becoming conic, becoming 35 mm deep and 42 mm wide with maturity, Yellow Green 144A in background with bracts Yellow 13B.

*Disc florets*.—To about 360 in number, each with 1 pistil and 4 stamen, grow to 10 mm long and 3 mm wide, each with one persistent, very stiff linear bract (16 mm long with the top 3 mm Yellow 13B to 7 mm Yellow Green 144A to 6 mm of White NN155A on bottom); corolla 5 mm long and 2 mm wide, tubular, 5 lobed, glabrous and glossy, Yellow Green 144A at the base to Yellow Green 149D; pistil 6 mm long, ovary 4 mm long, White NN155D with top Yellow Green 144A, style 5.5 mm long and Yellow Green 149D, 2-branched stigma spreading 3 mm wide, Yellow Green 149D on bottom half and tinted Greyed Purple N186A on top half; stamen 4.5 mm long, filaments 2 mm long and White NN155B, anthers 3 mm long and Greyed Purple N186B, pollen none.

*Involucral bracts*.—In 4 leafy series, area grows to 30 mm wide and 10 mm deep, lobes lanceolate in shape, reflexed, grow to 12 mm long and 3 mm wide, both sides Green 137A, margins strigose, tip acute, strigose on both sides.

*Receptacle*.—Grows to 14 mm wide and 23 mm deep, White NN155B.

*Bloom period*.—June through October in Canby, Oreg.

*Fragrance*.—Slight, floral perfume.

*Lastingness*.—Each inflorescence lasts about two weeks in Canby, Oreg.

*Seeds*.—4 mm long and 2.5 mm wide, oval, Brown 200C.

*Fertility*.—Moderate.

Disease and pests: No pests or diseases have been observed on plants grown under commercial conditions in Canby, Oreg. No resistances are known.

I claim:

1. A new and distinct *Echinacea* plant as herein illustrated and described.

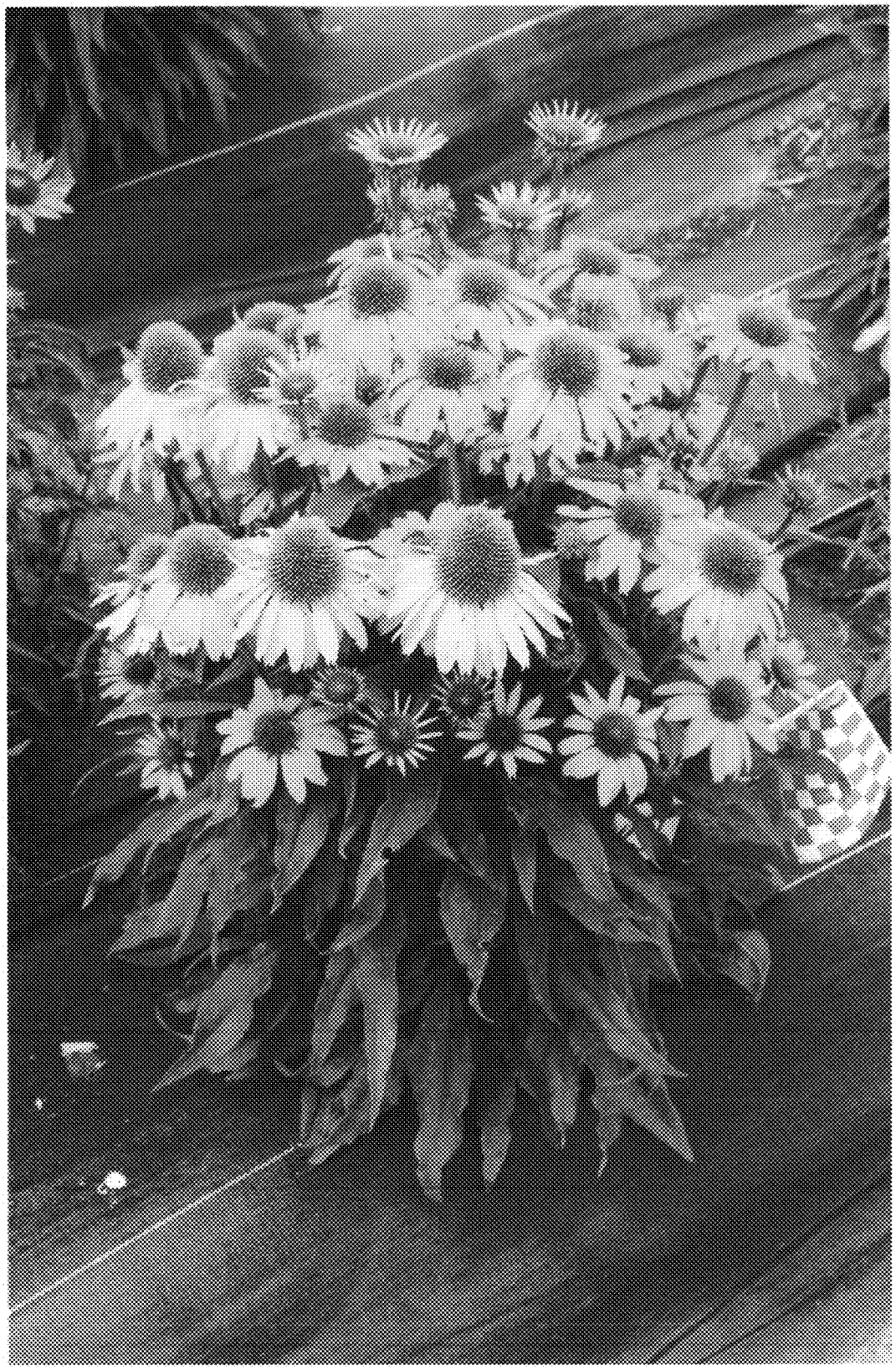

* * * * *